United States Patent [19]
Gehrke et al.

[11] Patent Number: 5,603,955
[45] Date of Patent: Feb. 18, 1997

[54] ENHANCED LOADING OF SOLUTES INTO POLYMER GELS

[75] Inventors: Stevin H. Gehrke, Cincinnati, Ohio; E. C. Lupton, Boston; Matthew E. Schiller, Waltham, both of Mass.; Lorelle Uhden, Cincinnati, Ohio; Nitin Vaid, Kanpur, India

[73] Assignee: University of Cincinnati, Cincinnati, Ohio

[21] Appl. No.: 276,462

[22] Filed: Jul. 18, 1994

[51] Int. Cl.⁶ .......................... A61K 9/10; A61K 47/32; A61K 47/34; A61K 47/36
[52] U.S. Cl. .................... 424/484; 424/486; 424/488; 424/487; 514/944; 252/315.2; 252/315.4; 252/315.3
[58] Field of Search ..................................... 424/484, 486

[56] References Cited

U.S. PATENT DOCUMENTS

| | | |
|---|---|---|
| 3,458,622 | 7/1969 | Hill . |
| 4,474,751 | 10/1984 | Haslam et al. ............... 424/78 |
| 4,474,752 | 10/1984 | Haslam et al. ............... 424/78 |
| 4,555,344 | 11/1985 | Cussler ....................... 210/670 |
| 5,252,318 | 10/1993 | Joshi et al. ................. 424/78.04 |

FOREIGN PATENT DOCUMENTS

| | | |
|---|---|---|
| 0178665 | 4/1986 | European Pat. Off. . |
| 1925919 | 11/1969 | Germany . |
| 3400106 | 7/1985 | Germany . |
| 2177708 | 1/1987 | United Kingdom . |
| 9213566 | 8/1992 | WIPO . |

OTHER PUBLICATIONS

Harsh, "Controlling Swelling Behavior of Novel Cellulose Ether Hydrogels", Dissertation, University of Cincinnati, pp. i–v; 1–136 (1992).

Kim et al., "Hydrogels: Swelling, Drug Loading and Release", Pharmaceutical Research, vol. 9, No. 3, pp. 283–290 (1992).

Peppas, "Hydrogels in Medicine and Pharmacy", vol. II Polymers, pp. 115–160 (1987).

Kamath et al., "Preliminary Study on the Controlled Delivery of a Bioactive Protein From Dextran Hydrogels", Proceed. Intern. Symp. Control. Rel. Bioact. Mater., 20 (1993), Controlled Release, Society, Inc., pp. 111–112.

American Chemical Society, "Polymeric Materials Sciences and Engineering", Proceedings of the ACS Division of Polymeric Materials: Science and Engineering, vol. 63, pp. 329–336, Fall Meeting, Washington, DC, 1990.

Antonsen et al., "Controlled Release of Proteins from 2–Hydroxyethyl Methacrylate Copolymer Gels", Biomat., Art. Cells & Immob. Biotech., 21(1), 1–22 (1993).

Gehrke et al., "Enhanced Protein Loading in Hydrogels", Proceed. Intern. Symp. Control. Rel. Bioact. Mater., 20, pp. 113–114, 1993.

Gehrke et al., "Protein Isolation by Solution–Controlled Gel Sorption", Biotechnol. Prog., pp. 355–358, 1991.

Gehrke et al., "Isolation of Proteins by Selective Gel Sorption", Extended Abstracts of American Institute of Chemical Engineers, 1992 Annual Meeting, 153i.

Gref et al., "Biodegradable Long–Circulating Polymeric Nanospheres", Science, vol. 263, pp. 1600–1603, Mar. 18, 1994.

Skuse et al., "Hydroxypropl Cellulose/Poly(ethylene Glycol)–Co–Poly(Propylene Glycol) Aqueous Two–Phase Systems: System Characterization and Partition of Cells and Proteins", Enzyme Microb. Technol., vol. 14, Oct. 1992.

Gehrke et al., Chemical Abstracts, vol. 115, 1992, #69868.
Gehrke et al., Chemical Abstracts, vol. 119, 1994, #233,955.
Gehrke et al., Chemical Abstracts, vol. 112, 1991, #164791.
Palasis et al., Chemical Abstracts, vol. 116, 1993, #91247.
Harsh et al., Chemical Abstracts, vol. 119, 1994, #79961.
Gehrke et al., Chemical Abstracts, vol. 119, 1994, #233955.

*Primary Examiner*—Edward J. Webman
*Attorney, Agent, or Firm*—Choate, Hall & Stewart

[57] ABSTRACT

A method of loading a drug into a crosslinked polymer network and protecting the drug from the effects of inactivation is described. The method includes the steps of contacting of a biologically active solute (i.e., drug) with:(i) a gel network; (ii) a second protectant polymer that is somewhat immiscible with the gel; and (iii) a protectant salt, under conditions sufficient for the biologically active solute to selectively partition into the gel and the protectants to be entrained in the gel. Most preferably, the gel network is a crosslinked gel responsive to a change in an environmental condition to which the gel is exposed.

15 Claims, 1 Drawing Sheet

ENHANCED LOADING OF SOLUTES INTO POLYMER GELS

BACKGROUND OF THE INVENTION

Three-dimensional polymer gel networks have been widely studied for use as delivery vehicles for a variety of solutes most particularly biologically active solutes.

Many methods of loading gels with solutes are presently available. Two of them relevant to drug loading include: (i) formation of the hydrogel in the presence of the solute (e.g., drug); and (ii) swelling of a preformed gel in a concentrated solution of the solute (e.g., drug). See, for example, Kim et al., *Phar. Res.* 9:283–289 (1992). Maximum loadings of high molecular weight solutes are generally on the order of about a few percent by weight of gel. Each of these techniques has serious limitations. In the first method, side reactions are possible between moieties reacting to form the hydrogel and the drug and it is often not possible to remove extractable materials from the gel after its formation without also extracting the drug. In the second method, solubility limitations become a drawback. That is, many drugs are sparingly soluble in water, and drug loading must be accomplished in non-aqueous solvents or water/solvent solutions. Since most naturally-occurring proteins, and proteins obtained from recombinant DNA techniques, are denatured or otherwise inactivated in non-aqueous solvents, this second method is not suitable for loading many biologically active materials. Moreover, large molecular weight materials (e.g., polypeptides) may be physically excluded from the hydrogels.

Partial denaturation of solutes such as vitamins, enzymes and the like is sometimes tolerated in purification/separation procedures since various methods have been developed to renature, or at least, reactivate the biologically active solute(s) once it has been purified. See, for example, Knuth and Burgess, "Purification of Proteins in the Denatured State", *Protein Purification: Micro to Macro*, pp. 279–305, Alan R. Liss, Inc., 1987. In separation/purification procedures protection of a particular solute (e.g., isolated enzyme, protein, vitamin) from inactivation during purification/separation procedure is preferred. In the drug delivery arts, it is counterproductive to even partially denature a biologically active solute once it is disposed on, or in, a delivery device since the solute must function when released.

Gref et al., *Science*, 263:1600–1602 (1994) have developed biodegradable nanospheres using amphiphilic co-polymers that phase-separate during emulsification. Loadings up to 45 percent by weight of a biologically active solute were achieved by dissolving the solute in the same organic solvent that dissolved the copolymer. Although loading is high using this method, the solute must be dissolved in a possible denaturant, i.e., an organic solvent.

Significantly, high loadings may lead to deactivation in other ways. For example, it is known that high levels of insulin are often used for insulin implants and controlled release devices. Reactions between the insulin molecules that are at high concentration lead to agglomeration and subsequent denaturation of the insulin. Furthermore, the manufacture of gel-based delivery devices will often require a drying step if the loaded gels are to be stored in their dry state between manufacture and use. Denaturation of the biologically active solute can also occur as a result of drying the gel.

What is required is a device and a method for loading effective amounts of solutes into polymer gel networks and that also avoid problems associated with denaturation or inactivation of the solute during, and after loading.

SUMMARY OF THE INVENTION

The present invention is based, on the discovery that: (i) unexpectedly high loadings; up to forty percent mass solute/polymer gel mass, can be obtained by modifying a two phase aqueous extraction protein purification method; and (ii) methods for maintaining activity of a solute of choice from denaturation within a crosslinked gel may be accomplished by trapping protectant moieties directly into the crosslinked gel. Both aspects of the invention are accomplished in a single step and can work synergistically.

One aspect of the invention is a method of loading polymer a solute into a crosslinked polymer gel network. The method includes the steps of contacting the biologically active solute with: (i) a gel network that incorporates a solvent; and (ii) a loading polymer that is soluble in the same solvent as the polymer, under conditions sufficient for the solute to selectively partition into the gel and for the solute to retain its activity within the gel. Most preferably, the solute is a biologically active solute and the crosslinked gel is a gel responsive to a change in an environmental condition to which the gel is exposed. The loading polymer may be a linear or branched polymer. A salt is preferably included to enhance partitioning of the solute into the gel.

A further embodiment is a method for delivering a preferred biologically active solute to an environment of use. The method includes partitioning at least one biologically active solute into a responsive polymer gel by the methods of the inventions and then triggering an expansion or collapse of the polymer gel under conditions sufficient to release at least one biologically active solute into the environment of use.

Compositions of the invention include three-dimensional, responsive polymer gel networks containing a protectant moiety and an amount of solute equal to as much as forty percent mass solute/polymer gel mass. The gel networks are made by contacting of the solute with: (i) a gel network; (ii) a loading polymer that is somewhat immiscible with the gel; and (iii) a optionally, a salt. Conditions are chosen so that the solute selectively partitions into the gel. The gel is then separated from the other components.

In preferred embodiments of the invention, the network is a responsive polymer gel and the protectant moiety is a salt or a linear polymer, either alone or in combination. The compound is a biologically active solute which may be a solute having a molecular weight greater than about 1,000 and is preferably selected from the group consisting of proteins, polypeptides, nucleoproteins, glycoproteins and lipoproteins.

Another embodiment of the invention are hydrogels whose water soluble polymeric starting materials can be used in the method of the invention. Exemplary materials include polyethylene oxide, polyethylene glycol, polyvinylalcohol, methylcellulose, dextran, hydroxypropyldextran and ethylhydroxyethylcellulose, and polyvinylpyrolidone, hydroxypropylcellulose, hydroxypropyl starch, and polypropylene glycol.

A drug delivery system is also included within the scope of the invention and comprises a polymer gel network including the drug to be delivered; a salt; and a loading polymer. The salt and the loading polymer are capable of protecting the drug from loss of activity. The polymer gel network is capable of expanding or collapsing in response to a change in an environmental condition to which the gel is exposed, the expanding or collapsing sufficient to release the drug into an environment of use.

A further embodiment of the invention is a wound dressing comprising a responsive polymer network having incorporated therein a medicament and a protectant, the network constructed such that a change in an environmental condition to which the gel is exposed releases the medicament to a wound site. Preferred responsive polymer networks for use in wound dressings include a medicament to be delivered; a salt; and a loading polymer, the salt and the loading polymer capable of protecting the medicament from loss of activity while in the wound dressing.

An iontophoretic drug delivery system of the invention comprises a polymer network including a drug to be delivered; a salt; and a loading polymer. The salt and the loading polymer are capable of protecting the drug from loss of activity.

A method of maintaining activity of a solute in a crosslinked polymer gel network is also described. The method includes introducing a protectant molecule and a solute that has biological and/or chemical activity into a polymer by contacting a solution of the solute with a gel and a protectant solution comprising a loading polymer and a salt where the loading polymer may be subjected to be the protectant. The contacting step is performed under conditions sufficient for the solute and the protectant molecules to selectively partition into the gel so that the activity of the solute is maintained during and after partitioning.

A variety of controlled release devices incorporate loaded responsive polymer gels of the present invention. One device includes the gel of the invention and is adapted to deliver a pest control substance when exposed to a change in an environmental condition. Another device is adapted to deliver a cleaning substance selected from the group consisting of an enzyme, a detergent, a bleach, when exposed to a change in an environmental condition. Yet another device is adapted to deliver an organic solvent, when exposed to a change in an environmental condition.

The invention has significant advantages. Common solvents, such as water, may be used in which all components are sufficiently soluble. Complete incompatibility and immiscibility of gel and loading polymers using the present technique is not required since the crosslinked polymer gel is always readily separable from the surrounding solutions. The gel protects labile solutes from denaturing conditions present outside the gel. The technique is readily generalizable to more than one gel phase multiple loading polymers, and different solutes.

It is therefore an object of the invention to provide a method of loading pharmaceutically-effective amounts of solute (up to forty percent mass solute/polymer gel mass) into a crosslinked gel.

It is a further object of the invention to provide a method for protecting a solute while the solute is within a crosslinked gel.

It is another object of the invention to provide a method for trapping protectant moieties directly into a crosslinked gel and loading the gel with a biologically active solute in a single step.

It is another object of the present invention to provide a gel delivery system that overcomes the limitations of solute size on loading into hydrogels.

It is a further object of the invention to provide a gel for solute release that can be designed for optimal release independent of conditions for effective loading of the solute.

BRIEF DESCRIPTION OF THE DRAWING

The novel features of the invention both as to its structure and operation is best understood from the accompanying drawing, taken in conjunction with the accompanying description, in which similar reference characters refer to similar elements, and in which.

DETAILED DESCRIPTION OF THE INVENTION

Figure 1:
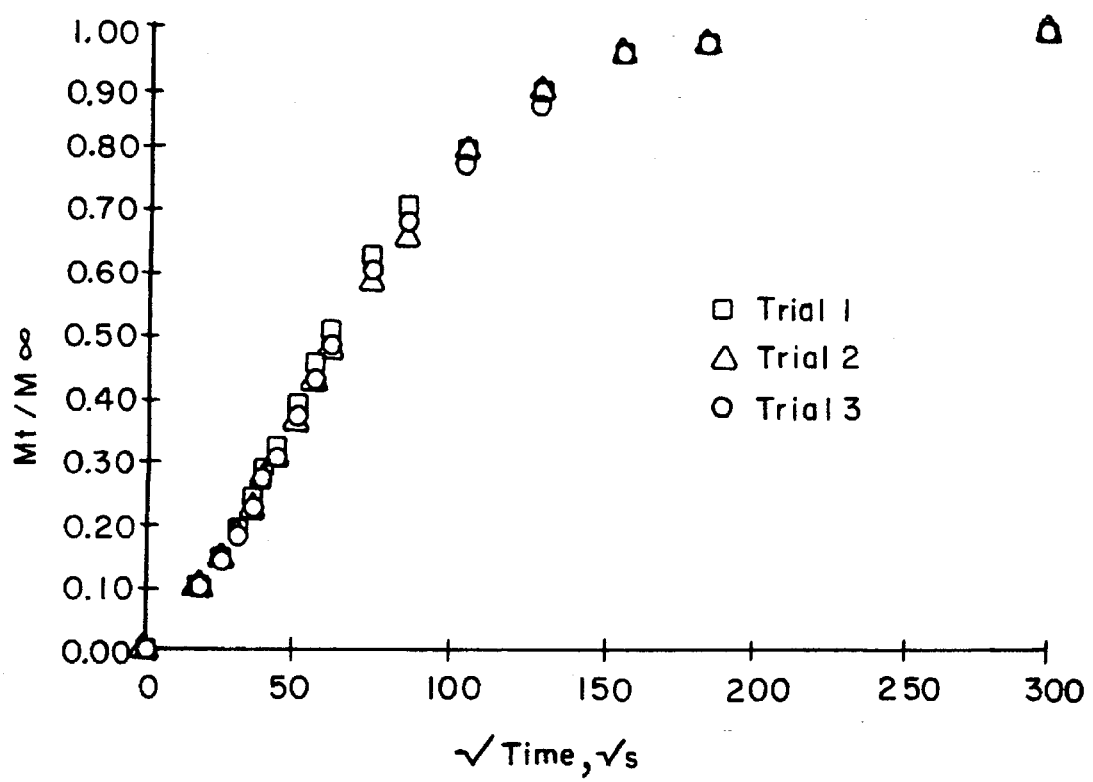
FIG. 1 illustrates release kinetics of amylase from a dextran gel. The Y axis is the release at a given time divided by total amount released at equilibrium.

The present invention pertains to methods of loading solutes, most preferably biologically active solutes, into polymer gels, the resulting polymer gels, and methods of using the loaded polymer gels. The term "enhanced loading" of solutes refers to our discovery that we can, in a single step, obtain loadings of large or small solutes into a crosslinked polymer gel and establish a gel environment conducive to maintaining the activity of the solute while it is in the gel. These two objectives, both of significance in the drug separation/purification and drug delivery arts, may simultaneously be accomplished by sorption of a solute into a gel, the sorption driven by addition of a water soluble, loading polymer to the solution containing the solute. It is preferred that a salt be also included in the solution. The presence of the salt and loading polymer have a synergistic effect which causes enhanced and selective partitioning (up to 40% mass solute/mass polymer gel) of the biologically active solute into the gel. Moreover, the same salt and loading polymer may be chosen as protectants to enter the gel.

The term "protectant" is meant to refer to materials that enhance the stability of the biologically active solute within the gel. For instance, it is well-known to stabilize enzymes with, for example, glycerol or other polyhydroxylated solutes such as polyethylene glycol, polypropylene glycol, and the like, or with sugar or sugar solutions (e.g., glucose, sucrose, fructose). In fact, in certain cases high protein concentrations by themselves may be their own protectants since the higher the protein concentration relative to buffer salts, the more it will act as a buffer itself. Using the present method, we have shown that biologically active solutes retain their activity after heat stress and after being released from the gel.

The present method is a modification of two-phase aqueous extraction methods for purifying proteins. In conventional two-phase aqueous extraction methods, a protein is made to selectively partition into one of two substantially immiscible aqueous polymer solution phases which are in contact with each other. This selective partitioning behavior is governed by properties such as molecular weight of the polymers and biologically active solute, the type and concentration of salts and the relative hydrophobicity/hydrophilicity of the biologically active solute. Differences in the various interaction energies between the biologically active solute and the different polymers leads to a partition coefficient (i.e., concentration of biologically active solute in the gel/concentration of the biologically active solute in the loading polymer) greater than one (i.e., preferential loading by the gel) or less than one (i.e., preferential loading by the loading polymer).

Gehrke et al., *Biotechnol. Prog.*, 7:355–358 (1991) have shown that this conventional protein purification process can be extended to situations in which the gel is crosslinked dextran gel beads. This may be problematic since crosslinked polymer gels generally would be expected to exclude larger molecular weight proteins from within the gel network. See, for example, Cussler, U.S. Pat. No. 4,555,344.

A. Enhanced Solute Loading of Crosslinked Polymer Gels

A method for loading solutes into crosslinked gels is as follows: A crosslinked gel network is optionally pre-equilibrated with a solute-free, loading polymer solution. The gel is then separated from the loading polymer. To each crosslinked gel, a solution (with the same loading polymer concentration as the pre-swelling solution) including a solute to be loaded is added. The system is then agitated to mix the gel and the solute mixture. Most preferably, a salt is also added to the solute-containing solution. The gel is separated from the remaining solution. The solute concentration remaining in the loading polymer may be determined by a variety of methods, depending upon the solute of interest. For example, in spectrophotometric assays, light absorbance is measured at 280 nm for proteins; at 630 nm for blue dextran; and at 520 nm for Vitamin B12 with a UV/VIS spectrophotometer. The concentration of solute in the gel is determined by a mass balance. We have used dextran beads (Sephadex, registered TM) that are designed for gel filtration or size exclusion chromatography as the gel. These gels are sold specifically for their protein excluding capabilities.

Preliminary partitioning experiments have been performed using crosslinked dextran beads. Prior to the protein partitioning experiments, dry gels were pre-swollen with biologically active solute-free PEG solution. Enough of the dried Sephadex gel beads were added to fritted glass centrifugation tubes to obtain about 0.6 g of gel when swollen. The centrifuge tubes were then fitted into plastic test tubes and 3 ml of PEG solution was added to each; 15 minutes was found to be sufficient for equilibration of the gel and the solution. Centrifugation (IEC Clinical Centrifuge) at roughly 400 RPM for 60 minutes was used to separate the supernatant from the swollen beads.

To each tube of pre-swollen gel, 1 ml of solution with the same PEG concentration as the pre-swelling solution but including the test biologically active solute was added. The tube was then agitated manually for a few minutes to allow mixing of swollen gel and solution. Equilibrium of the protein and the gel was reached in several minutes and the gel was separated from the supernatant as before. The protein concentration in the PEG was determined by measuring light absorbance at 280 nm for proteins, at 630 nm for blue dextran and at 520 nm for Vitamin B12 with UV/VIS spectrophotometer (Shimadzu UV160U). The concentration of biologically active solute in the gel was determined by a mass balance Solutes are recovered from the loaded gel as follows: The solute is chosen to have a very low partition coefficient in pure buffer lacking any polymer. The solute contained in the loaded gel after the partitioning experiment is recovered by adding pure buffer lacking any polymer to the loaded gel. If in bead or particulate form, the gel may be separated by centrifugation from any supernatant. Otherwise, the gel is simply removed and blotted free of solution. The concentration of the solute in the supernatant is measured using a spectrophotometer. This procedure is repeated until the solute concentration in the supernatant is negligible.

With a reversibly responsive gel, recovery of loaded solutes may be accomplished by causing the gel to undergo volumetric collapse using established methods. See for example, Cussler, U.S. Pat. No. 4,555,344, incorporated herein by reference.

Persons having ordinary skill in the art may readily use the methods described herein to test the effectiveness of particular polymers in separation and the effect of salts on the partition coefficient. Measurement of retention of biological activity of biologically active solutes is also readily accomplished using the general protocol developed herein by releasing the biologically active solute from the gel and assaying its activity. Depending on the biologically active solute, a variety of conventional assays (e.g., spectrophotometric, immunoassay, and the like) may be developed that are well within the skill level of those in the art.

Results of work presented here are summarized.

1. Dextran gel cylinders loaded with amylase using polyethylene glycol and KCl as protectants retained the amylase activity even when the loaded gel was maintained at 60 degrees C.

2. Release kinetics of amylase and ovalbumin from loaded cylindrical gels of the invention show a typical diffusion controlled release.

3. Surface adsorption of biologically active solutes in the gels is not a significant factor in loading gels and the solutes are primarily incorporated within the gel network. The clearest proof of this are the experiments performed on non-bead gels which clearly show penetration of solute and diffusion controlled release from within the gel. (see FIG. 1).

4. HPC—similar results were seen in two different cylinders.

DESIGN RULES: SELECTION OF COMPONENTS

1. Salts:

A. Effect on Loading—A "salt" is defined herein as a substance that ionizes or dissociates completely when dissolved in water to produce a solution containing ions, which ions include positive cations (but not $H^+$) and negative, non-metal or amphoteric anions (but not $OH^-$).

The variation of salt type and salt concentration provides some guidelines by which selectivity and yield of solute loading can be manipulated to load a first crosslinked polymer gel with amounts of, for example, a protein that can be pharmaceutically effective. Salts affect biologically active solute loading through hydrophobic and ionic interactions, and this implies that the change in the partition coefficient due to the presence of salts will primarily be dependent on the hydrophobicity and charge on the biologically active solute and on the interfacial potential difference between gel and loading polymers.

Johansson, G., "Partitioning of Proteins", in *Partitioning in Aqueous Two-Phase Systems*, (Walter et al., eds.), Academic Press, New York, 1985, incorporated herein by reference, has derived a nomograph depicting the virtual partition coefficients of different ions in two phase aqueous protein extraction. Sorption by one of two aqueous phases is favored by addition of salts in the increasing order lithium-ammonium-sodium=cesium-potassium for cations and in the increasing order phosphate-sulfate-acetate-fluoride-chloride-bromide-iodide-thiocyanate-perchlorate for anions.

One would not necessarily expect that these design rules for aqueous extractions would be applicable to the present methods using crosslinked polymer gel phases because proteins are generally excluded from gels. Also, a crosslinked gel-loading polymer-water phase diagram might differ from a polymer-polymer-water phase diagram. Nevertheless, these design rules may also be used as guidelines to select a salt for a particular biologically active solute loading scheme of the present invention.

Two salts can be compared by comparing the value of the virtual partition coefficients of the cation and anion (Log $K_+$–Log $K_-$). For a positively charged biologically active solute (e.g., protein) a greater value of (Log $K_+$–Log $K_-$) implies greater partitioning into a crosslinked gel. For a negatively charged protein, the opposite effect is observed; that is, a smaller value of (log $K_+$–Log $K_-$) implies greater partitioning into the gel polymer. The magnitude of this effect depends on the magnitude of charge on the protein; therefore, by changing the pH of the system such that the protein charge increases (i.e., made either more positive or negative), the effect of the presence of that salt can be enhanced.

The choice of a preferred cation is made on the basis that the K values obtained should be greater than one because the aim was to enhance loading of proteins into the gel rather than exclude the proteins from the gels. In order to get K>1, the value of (log $K_+$–log $K_-$) for a negatively charged protein must be positive, and for a positively charged protein the value must be negative. We used this rule where the cation for the case of negatively charged ovalbumin was $K^+$ (salts were KF, KCl, KBr, KI) and the cation for the case of positively charged ovalbumin was $Bu_4N^+$ (salts were $Bu_4NF$, $Bu_4NCl$, $Bu_4NBr$, $Bu_4NI$). The partition coefficients obtained from the above experiments for different anions are presented in Tables 1 and 2. For negatively charged ovalbumin, K increases in the order $F^-<Cl^-<Br^-<I^-$, whereas for positively charged ovalbumin, K decreases in the same order. Tables 1 and 2 show the importance of sign of the charge on the protein. For example, in the presence of $I^-$ ovalbumin favors the gel when it is negatively charged but favors the PEG when the charge on it becomes positive.

TABLE 1

Effect of Anions on Negatively Charged Protein

| Salt (0.05M) | KF | KCl | KBr | KI |
|---|---|---|---|---|
| Partition Coefficient (K) | 2.6 ± 0.4 | 5.5 ± 0.8 | 7.0 ± 1.1 | 8.7 ± 1.2 |

TABLE 2

Effect of Anions on Positively Charged Protein

| Salt (0.05M) | $Bu_4NF$ | $Bu_4NCl$ | $Bu_4NBr$ | $Bu_4NI$ |
|---|---|---|---|---|
| Partition Coefficient (K) | 7.8 ± 1.3 | 3.1 ± 1.5 | 2.5 ± 0.5 | 1.7 ± 0.3 |

If two salts are present, the ratio of the salts determines the partitioning for salt concentrations in the range 0–250 mM. This property can be used to create a pH buffer which does not interfere with the partitioning. The partition-enhancing salt selected can be present in excess relative to the buffering salt, so that the partitioning is not affected by the buffering salt.

By the addition of a salt in a loading polymer, we have observed large values of K for ovalbumin. This increased partitioning in the presence of KI might be due to an unequal affinity of $K^+$ and $I^-$ ions for the dipoles present on the two polymers. This difference in affinity would result in the negatively charged ovalbumin being partitioned away from the loading polymer in order to maintain electroneutrality. Since the mechanism suggested for the effect of salts is based on the affinity of $I^-$ ions for the loading polymer, it is necessary for it to be present in solution for the salts to have the observed effect on the K value. The exact mechanisms by which salts enhance partitioning is not entirely clear.

At low salt concentrations, the buffering salt, the protein and the partition enhancing salt will contribute to the interfacial potential since they are charged molecules. This contribution will depend on the relative concentrations of these molecules. It is believed that, as the concentration of the partition enhancing salt increases, the contribution of the protein and the buffering salt to the interfacial potential will grow smaller and smaller. Therefore, the partitioning of the protein is expected to be increasingly determined by the partition of the partition enhancing salt as the concentration of the latter increases. This behavior predicts an increase in the partition coefficient as the concentration of the partition enhancing salt is increased.

B. Effect as Protectant—Salts are also selected on the basis of their protective properties. The particular salt chosen should ideally enhance loading and act as a protectant. It will be appreciated that selection of a salt will depend, in large part, on the solute to be loaded. It will be further understood that salts useful in partitioning may not be useful as protectants, so compromises must be found and experiments must be performed to test individual salts.

For example, potassium iodide (KI) is preferred to enhance loading (See above) but it is a chaotropic salt which tends to reduce hydrophobic interactions within the gel and within proteins. Chaotropic salts (e.g., guanidinium chloride) can denature proteins. Nevertheless, amylase released from HPC gels loaded using KI did maintain at least 40% of its activity (Example 5).

Salts such as ammonium sulfate $((NH_4)_2 SO_4)$ are known to stabilize hydrophobic interactions that hold proteins together and may be useful as a protectant salt.

POLYMERS: General Considerations

Polymers and polymer gels used in the methods of the present invention and described below may be selected from a variety of materials. In the broadest embodiment, gel and loading polymers of the invention may be selected from any one or more of a host of gels whose water soluble polymeric starting materials separate into two-phases. That is, in an aqueous system, multiples of these starting materials are fully water soluble yet are incompatible enough with each other so that they separate into two or more aqueous phases. Either one of the polymers of the phase system may be crosslinked and used as the gel. Moreover, either one of the polymers of the phase system may be used as a solution of loading polymer in the methods of the invention. Exemplary materials of this type include polyethylene oxide, polyethylene glycol, polyvinylalcohol, methylcellulose, dextran, glycerol, hydroxypropyldextran, hydroxypropylcellulose, hydroxypropyl starch, polypropylene glycol and ethylhydroxyethylcellulose, and polyvinylpyrolidone. There are additional polyphase systems of a similar nature. Exemplary materials meeting these requirements may be found in suitable reference work such as P. A. Albertsson, *Partition of Cell Particles and Macromolecules,* 3rd edition, J. Wiley and Sons, 1986, incorporated herein by reference. Polymers soluble in organic solvents may also be used.

2. Crosslinked Gel:

The term "gel" refers to a three-dimensional, crosslinked polymer network that includes a liquid solvent entrained by the interconnected matrix of polymer chains. The term "polymer network" refers to polymers crosslinked to create a three-dimensional, tangled network. The term "gel" more particularly refers to polymer networks between the liquid and solid state containing enough solvent molecules to cause macroscopic changes in the sample dimension. The term is also meant to include gels in their "dry" condition, in which all substantially all solvent that is within the gel matrix has been removed. The term dry is primarily an operational definition. One definition of the term is when the mass of the gel reaches a constant low value in desiccator or drying oven.

The concentration of gel may vary over a wide range. Preferred swelling degrees (Q=inverse of weight fraction) of gel range from Q=2 g/g to 100 g/g; most preferred are 4 g/g to 20 g/g.

In principle, multiple crosslinked polymers (i.e., two or more different crosslinked polymers) may be loaded using the methods of the invention. For example, a common solution of two, or more, different enzymes may be formulated and added to a mixture of corresponding (i.e., two or more) crosslinked polymer gels. By appropriate manipulation of polymers and salts as described herein, the different biologically active solutes may be partitioned into different crosslinked polymer gels with or without a third polymer.

Preferred gels are hydrogels that are well-known as being useful in controlled release applications. See, for example, Antonsen et al., *Biomat. Art. Cells & Immob. Biotech.*, 21: 1–22 (1993) and Gehrke and Lee, "Hydrogels for Drug Delivery Systems", in *Specialized Drug Delivery Systems*, p. 333 (ed. P. Tyle), M. Dekker, Inc., New York, 1990 and references cited therein.

Other preferred gels are derived from water soluble starting materials that will separate into two or more aqueous phases, as described above. Other preferred gels are three-dimensional polymer gel networks that are environmentally responsive. Responsive phenomena have been observed in permanently crosslinked polymer networks that exist as gels. As an external environmental condition (e.g., temperature; pH, ion concentration, light energy, solvent composition) is changed, the polymer network becomes increasingly compressible, and at a certain point, it becomes infinitely compressible. It was also observed that the volume of such a gel changes reversibly by a factor as large as several hundred when the gel is presented with a small change in external conditions such as solvent chemical composition or temperature. Tanaka, *Physical Review Letters.*, Vol. 40, no. 12, pp. 820–823, 1978 and Tanaka et al, *Physical Review Letters.*, Vol. 38, No. 14, pp 771–774, 1977; Tanaka et al *Physical Review Letters* 5, Vol 45, pg. 1636, 1980; Ilavsky, *Macromolecules.*, Vol. 15, pg. 782, 1982; Hrouz et al, *Europ. Polym. J.*, Vol. 17, pg. 361, 1981; Ohmine et al, *J. Chem. Physics*, Vol. 8, pg. 6379, 1984; Tanaka et al, *Science*, Vol. 218, pg. 462, 1982 and Ilavsky et al, *Polm. Bull.* Vol. 7, pg. 107, 1982; Gehrke, "Responsive Gels: Volume Transitions II"; ed. K. Dusek, Springer-Verlag, New York, pp. 81–144 (1993); Li et al., *Ann. Rev. Mat. Sci.*, 22:243–277 (1992); and Yu et al., *Enzyme Microb. Technol.*, 15:354–366 (1993), all of which incorporated herein by reference. Preferred responsive gels are "reversibly responsive", i.e., when challenged with an environmental change, the environmental change affects the gel by causing the entire gel, or a component thereof, to undergo a reversible volumetric change. The gel expands from a less liquid-filled state or dry state to a more liquid-filled state; or collapses from a more liquid-filled state to a less liquid-filled state. The reversible volume change involves a shift between two equilibrium states (i.e., swollen and collapsed).

Responsive gels may be "fast response" gels. As defined herein, "fast response" means that the gel reaches 90% of its maximum volumetric swelling or 90% of its minimum volumetric collapse in a time that is at least ten times faster than a comparable non-porous gel of the same geometry when both gels are subjected to a similar change in an environmental condition. Methods of making and using fast response gels may be found in co-pending and commonly assigned PCT application, Ser. No. PCT/US94/05400, filed 13 May 1994 (35 U.S.C. Section 371(c) (2): "Microporous Fast Response Gels and Methods of Use"—Gehrke and Kabra), incorporated herein by reference.

Many of the fast response gels are microporous. The term "microporous" refers to two-phase systems of a continuous solid phase containing numerous pores filled with fluid. A "microstructure" as defined herein, refers to those structures of a gel (e.g., pores, voids, walls and the like) observable under a scanning electron, or other, microscope and ranging in size from 0.01 to about 100 microns. Gels containing pores in the size range 0.01 to about 10 microns are 'microporous'. If some of the pores are interconnected, the gel is typically called an "open-cell" gel. If all the pores in the gel are interconnected to each other, the gel is a "bicontinuous" gel. If the pores are discrete (not connected to each other), so that the internal space of each pore is independent of the other pores, the gel is a "closed-cell" gel. The present invention encompasses as all these morphological forms and combinations of these forms.

The primary requirement of a responsive gel is that the entire gel, or a component, undergo a volume change. The gel as a whole must meet these requirements. Nevertheless, the gel may itself include several other components as long as at least one component(s) provides the required property. The second requirement of a gel used in the present methods is that the entire gel, or a component, be capable of sorbing a biologically active solute that is to be loaded.

For instance, the gel may be a single component such as a single polymer network which meets the requirement that the gel be responsive to an environmental change. The gel may also be a single component, such as a single polymer network which meets both loading and responsive requirements. An exemplary component is hydroxypropylcellulose.

The gel may also include two or more components, each component having a different required property. A primarily sorptive-type gel may also be made in the presence of a volume-change gel. Exemplary sorbents of this type include poly-N isopropylacrylamide [NIPA: "responsive component"]/poly(methacrylamidopropyltrimethylammonium chloride[MAPTAC: "loading component"]. A primarily loading-type gel may also be made in the presence of a responsive gel. The gel may also be an interpenetrating polymer network (IPN). An IPN may possess only a responsive property such as poly-N isopropylacrylamide. A purely responsive IPN may thus be combined with a loading gel to meet the requirements of the present system. A purely responsive IPN may itself be combined in an IPN with a "loading" component such as poly(MAPTAC). The IPN may possess both properties, however, so that one polymer member of the IPN provides the loading property and the other polymer member provides the responsive property. Polymers of an interpenetrating gel to be loaded can include natural polymers, synthetic polymers, or crosslinked natural and synthetic polymers. Examples of synthetic polymers include poly(acrylamide), poly(acrylic acid), and the like.

As discussed previously, an important advantage of combining different polymers as part of the loaded gel (see for example, the interpenetrating polymer networks described above) is that one member(s) of the gel may be chosen for its strong ability to undergo responsive volume change and the other member(s) may be chosen for maximum loading ability. In this regard, polymers of MAPTAC are extremely useful. By itself, poly(MAPTAC) is not a gel but will absorb large amounts of water. An enhanced capacity for loading one or more biologically active solutes into a responsive gel is facilitated by poly(MAPTAC) and delivery of the solution taken up by the poly(MAPTAC) is facilitated by the responsive gel component. The poly(MAPTAC) will not be delivered along with the biologically active solute because it is too large a molecule. Examples of gels utilizing poly(MAP- TAC) include, but are not limited to any of the reversibly responsive gels described previously such as poly-N isopropylacrylamide/poly(methacrylamidopropyltrimethylammonium chloride[MAPTAC])/water; poly(acrylic acid/poly(methacrylamidopropyltrimethylammonium chloride[MAPTAC])/water; and acrylamide-sodium acrylate/methacrylamidopropyltrimethylammoniumchloride/water. Polymers of MAPTAC may be combined with a responsive gel, either in an interpenetrating network, by copolymerization, or by synthesizing a responsive gel in the presence of poly(MAPTAC). Other polymers like poly(MAPTAC) that are not responsive gels but are useful for their liquid loading properties include polyvinylimidazole.

The volume change of the entire gel, or a component thereof, may be either continuous or discontinuous. A "continuous" volume change is marked by a change in volume (i.e. a collapse and/or swelling) that occurs over a relatively large change in environmental condition. Moreover, there exists at least one stable volume near the transition between the swollen and collapsed states.

Responsive gels may also undergo a "discontinuous" volume change in which the transition from swollen to collapsed states, and back again, occurs over an extremely small change in environmental condition, such as less than 0.1 degree C. or 0.1 pH unit. Such reversibly responsive gels have been called discontinuous "phase-transition" gels. See Tanaka et al. U.S. Pat. No. 4,732,930, or Hirotsu et al., *J. Chem. Phys.* 87: 15 July 1987 describing synthetic polymeric gels that undergo phase transitions, incorporated herein by reference. There is no stable volume between the swollen and collapsed states at the phase-transition and, in theory, the expansion and/or collapse occurs over an infinitely small environmental change. A gel undergoing a continuous volume change may have a similar order of magnitude total volume change as a gel undergoing a discontinuous change.

On a molecular level, the preferred responsive gels are sensitive to small changes in a restricted repertoire of environmental "trigger" conditions consisting primarily of temperature. Trigger conditions are not so limited, however, and may also include pH, solvent concentration, and ion concentration. On a macroscopic level, any of a variety of environmental conditions may be imposed on the gel which allows the specific trigger to induce a volume change. These environmental conditions may, but not necessarily, be the same as the trigger and include, but are not limited to, a change in temperature, electric field, photon energy, pH, solvent composition, ion concentration, concentration of biomolecules, pressure, and the like.

The responsive gels of the invention may be combined with a solute that acts as a molecular "transducer", converting an environmental condition into an appropriate trigger. For example, a dye may be introduced into a temperature-triggered fast response gel. The dye is designed to absorb light of a given energy and convert the light energy into heat, thus triggering the gel to undergo a temperature induced rapid phase-transition. See also, A. Suzuki and T. Tanaka, Nature: 346: 6282 (1990), incorporated herein by reference.

The volumetric changes of gels described herein result from competition between intermolecular forces, usually electrostatic in nature, that act to expand the polymer network; and at least one attractive force that acts to shrink it.

Volumetric changes in aqueous responsive gels are driven primarily by four fundamental forces: ionic, hydrophobic, hydrogen bonding and van der Waals bonding interactions, either alone or in combination. Each of these interactions may be independently responsible for a volume change in preferred gels of the invention. Each of these fundamental forces is most strongly affected by a particular trigger. Changes in solvent concentration most strongly affect the van der Waals interaction; changes in temperature most strongly affect hydrophobic interactions and hydrogen bonding; and changes in pH and ion concentration most strongly affect ionic interactions.

Thus, a responsive gel whose volume change is governed by ionic interactions would include components that are weakly acidic and weakly basic, such as poly(acrylic acid)/[MAPTAC])/water; poly(acrylic acid)/poly(allylamide)/water, and the like. See, Siegel and Firestone, *Macromolecules,* 21: 3254–3259 (1988). Gels of this type are sensitive to pH and will collapse when exposed to a lower pH environment from a higher pH environment.

Responsive gels whose volume change is governed by hydrogen bonding will collapse with a decrease in temperature and are exemplified by interpenetrating polymers that comprise poly(acrylic acid) as one polymer, poly(acrylamide) as the other polymer, and water as the liquid medium. Gels whose volume change is governed by hydrophobic interactions will collapse when challenged with an increase in temperature and are exemplified by poly(N-isopropylacrylamide:NIPA). See U.S. Pat. No. 4,863,613. Gels whose volume change is governed by van der Waals interactions will behave similarly to those governed by hydrophobic interactions and are exemplified by polyacrylamide gels.

Responsive gels may be formulated in which the volume change is governed by more than one fundamental force. In particular, gels consisting of copolymers of positively and negatively charged groups meet this requirement. In these gels, polymer segments interact with each other through ionic interactions and hydrogen bonding. The combination of these forces results in the existence of several pH-driven phases. See Annaka and Tanaka, *Nature.* 355: 430–432 (1992), incorporated herein by reference. An exemplary gel of this type is a copolymer of acrylic acid and methacrylamidopropyltrimethyl ammonium chloride (MAPTAC).

Equations qualitatively explain all of these aspects of volumetric changes. See T. Tanaka, D. J. Fillmore, S. T. Sun, I. Nihio, G. A. Swilslow, and A. Shar, *Phys. Rev. Letters.,* 45 1636 (1980) and U.S. Pat. No. 5,100,933 (Tanaka et al.), incorporated herein by reference. See also, S. H. Gehrke, *Adv. Polymer Science* 110:81–144 (1993), for other theoretical descriptions.

Representative crosslinking agents useful for making the crosslinked gels to be loaded include N,N'-methylene-bis acrylamide, ethylene glycol dimethacrylate, glycerine triacrylate or divinylbenzene or the like. The concentration of crosslinkable solute is generally about 0.3 to 4 mole percent based upon the polymerizable solute which is the main component. The crosslinking agent effects partial crosslinking of the polymer and provides a means to control the gel's mechanical strength, swelling degree, and intensity of phase transition trigger by changing the crosslinking density. Crosslinking of linear polymers by chemical reagents is preferred for gels made from biological polymers such as cellulose ethers. See Gehrke and Lee, supra.

Specific crosslinkers will depend upon the polymer but preferred crosslinkers for polysaccharide gels, especially cellulose ethers, are multifunctional carboxylic acids, such as adipic acid (hexanedioic acid: $HOOC(CH_2)_4COOH$), succinic acid ($HOOC(CH_2)_2COOH$), malonic acid (propanedioic acid:$CH_2(COOH)_2$, sebacic acid (decanedioic acid: $HOOC(CH_2)COOH$), glutaric acid (pentanedioic acid:

HOOC(CH$_2$)$_3$COOH), or 1,10 decanedicarboxylic acid. Dicarboxylic hydroxyacids such as tartaric acid and malic acid as well as multifunctional carboxylic acids such as 1,2,3,4-butanetetracarboxylic acid may also be suitable. Unsaturated dibasic acids have been used to physically crosslink water soluble polymers by application of drying and/or heat. See, for example, U.S. Pat. No. 3,379,720 (Reid), incorporated herein by reference. Unfortunately, the heat required to crosslink water soluble polymers within a reasonable time of several hours is very high, ranging from 90° C. (2–3 hour gelation) to 200° C. (1–2 minute gelation). This may render the Reid method unsuitable for use with heat labile, biologically active compounds. At room temperature, the Reid methodology produced a gel in 10–30 days.

We have discovered that a preferred method of effective crosslinking may be accomplished in 3–4 hours by using acyl halide derivatives of multifunctional carboxylic acids as the reagents added to the polymer solution. These acyl halides preferably are chloride derivatives such as adipoyl chloride, sebacoyl chloride, succinyl chloride, and the like. Acyl chloride derivatives of multifunctional carboxylic acids are very unstable in water and will react almost immediately to form the corresponding acid in solution (e.g., S. H. Pine et al., *Organic Chemistry*, supra, p. 319) and it is this acid, not its halide derivative, that becomes incorporated into the final form of the polymer network as the crosslinkage. Furthermore, because the halide derivative is so reactive with water, aqueous leaching of a polymer network with any residual halide derivative will necessarily yield the acid form of the crosslinker in the leachate, not the halide derivative.

Polymerization is initiated using a polymerization initiator, e.g., a free radical initiator such as ammonium persulfate or sodium metal bisulfite, etc., with dilution with a solvent, e.g., water, a lower alcohol, hydrocarbon, etc., or without dilution. However, neither the solvent nor the polymerization initiator are always important factors to obtain the polymerized product from the monomer mixture, and any method suitably selected from conventionally well-known gelation methods may be applied. Crosslinking can also be induced by ultraviolet or electron beam irradiation.

Crosslinked polymer networks may also be affixed onto a matrix or membrane. See Example 1. Thus, networks of the invention may be loaded and simultaneously affixed to, for example, a matrix designed for transdermal drug release. Crosslinked polymer networks may also be affixed onto a matrix or membrane after loading and fabricated into a variety of forms. For example, the materials may be used in support matrices, films or membranes, tubes, hollow fibers, solid fibers, molded objects, solid particles, capsules, micelles or liposome-like structures.

3. Loading Polymer:

A. Effect of Loading—The loading polymer may be any polymer soluble in an aqueous phase. Preferably, the loading polymer is also soluble in the same solvent that is the solvent of the gel. Water is a particularly preferred solvent although the solvent may be nonaqueous.

The loading polymer may also be crosslinked, into a gel. In any case, there needs to be at least a continuous solvent phase between first and loading polymers to allow transport of at least one solute from one polymer to the other polymer that is to be loaded.

It is preferred that the gel and loading polymer be chemically and physically incompatible-e.g., the gel is more or less hydrophobic than the loading polymer so that they will not form a solid solution in each other at their respective concentrations.

There are a number of immiscible polymeric materials that are mainly water and that are close to each other on a spectrum of relative hydrophobicity-hydrophilicity. This means that systems formed by these polymers can be expected to be selective in separating substances which themselves are mainly water; that is substances that fall within the same part of the solvent spectrum. Examples of these are particles and macromolecules of biological origin. Aqueous solutions of the following polymeric materials are mutually immiscible and are ranked in rough order of increasing hydrophobicity: dextran sulfate, carboxymethyl dextran, dextran, hydroxypropyldextran, methylcellulose, hydroxypropylcellulose, polyvinylalcohol, polyethylene glycol and polypropylene glycol. Thus, any two of these may serve as the first and loading polymers. There are many published examples of such systems. See, for example, P. A. Albertsson, *Partition of Cell Particles and Macromolecules*, 3rd edition, J. Wiley and Sons, 1986. These simple design rules may be tested using methods described herein.

With properly chosen polymer systems, all manner of solutes may be loaded using the present methods. Data shown in P. A. Albertsson (supra, p. 288) for a non-crosslinked dextran-PEG system include the organic solute 1-Naphthol (MW=460,000) which, along with its isomer 2-naphthol, are precursors to such drugs as the analgesic Naproxen and the Vitamin K family of solutes, especially Vitamin K$_5$. These solutes also have food preservative properties. The partition coefficient of 1-Naphthol (1.76) is significantly different from one. Based on our work with crosslinked gels, this demonstrates the possibility of successful loading of this solute into crosslinked gels with the properly chosen systems.

B. Effect as Protectant—The loading polymer may be chosen for action as a protectant. It is known that proteins in solution may be stabilized against aggregation, precipitation, and denaturation reactions using water soluble polymers, particularly hydroxyl-containing polymers such as polysaccharides (i.e., starch and cellulose ethers), polyethylene glycol, polypropylene glycol, and copolymers thereof. See also Schein, C. H., *Bio/Technology*, 8: 308–317 (1990), incorporated herein by reference. Presence of the continuous liquid phase between the gel and loading polymer also allows some salt and loading polymer to become entrained within the gel.

One factor that determines the amount of loading polymer protectant and salt entering the gel is the degree of swelling of the gel in the loading polymer solution. For example, dextran gel beads will not swell as much in polymer solution as will a gel made of cellulose ether, e.g., hydroxypropylcellulose. The second determinant is the amount of loading polymer in solution; the more concentrated the loading polymer solution, the more it is absorbed into the gel. Thus, one may adjust the loading polymer solution concentration and the swelling degree of the gel.

1) Adjusting the amount of solute or protectant added to gel:

From a mass balance on the loading process, the total amount of solute or protectant added to loaded gel can be calculated as follows:

$$M_p/M_{gel}=(Q-1)\Sigma(i=1 \rightarrow n)k_i x_i$$

where:

$M_p$=total mass of solute or protectant in the loaded gel $M_{gel}$=mass of dry gel Q=mass swelling degree of gel in loading solution (swollen mass/$M_p$)

$k_i$=partition coefficient of species 'i'=ratio of mass fraction of 'i' gel to mass fraction of species (i) in loading solution $x_i$=mass fraction of 'i' in loading solution n=number of species For salts and inert (i.e. does not affect partitioning of bioactive solute) species, including protectants like glycerol and lactose, k will be approximately 1 (see P. A. Albertsson, Table 5.1, page 74). For the loading polymer, the value of k will be between 0 and 1. The phase diagram for the polymer-gel-water system will determine the value of k for the loading polymer, as well as the swelling degree of the gel (Q). The phase diagrams for 24 different systems is given in Chapter 12 in Albertsson, along with detailed directions for determining the phase diagram of any given system. For crosslinked gel-soluble polymer systems, determining the phase diagram is much easier than for the soluble polymer-soluble polymer systems. Polymer concentration assays can be avoided since there can be no gel polymer that is dissolved in the soluble polymer solution. The gel of known mass and water content is equilibrated with a comparable volume of loading polymer solutions of various compositions. The gel is removed and weighed to determine total mass, then dried to determine water and soluble polymer content. Similarly, the polymer solution is weighed, then dried to determine water content and thus polymer content. Other techniques are also possible; for example a gel of known dry mass can be swollen in excess polymer solution whose composition can be assumed constant, and then removed, weighed and dried to determine water and soluble polymer content. If salt is present in the systems, however, an assay for the salt or the solution polymer will also be required.

Using an approximate phase diagram giving estimates of Q and $k_i$, can one determine the concentrations of protectants needed to obtain the desired objective, while using salt and polymer selection rules to simultaneously obtain efficient protein loading.

There may well be other reasons for desiring the loading of adjunct materials into the gel along with the active solute. For example, a surfactant may help solubilize a poorly soluble drug, salts may alter the swelling rate of the gel and thus the release rate of the drug, and so on. The use of such additives in formulating a drug release system is well-known in pharmacy and other fields involving delivery of solutes to target environments.

2) Protocol for determining ability of protectants to retain or reduce the loss of bioactivity of a loaded solute a) Determine the appropriate assay for solute bioactivity.

b) Identify the likely denaturing event from which the solute is to be protected; e.g. temperature or pH, precipitation, agglomeration.

c) Prepare several solutions: a control of the active species in appropriate solution (typically one equal to the release solution), the same solution with different levels of protectants dissolved in it according to rules described herein.

d) Determine the bioactivity of the freshly prepared solute solution.

e) Set aside two aliquots of the control; then load the gel by immersion in the various test solutions, including an aliquot of the control solution.

f) Process the loaded gels as appropriate; e.g., dry under vacuum, heated, store wet, etc. and treat a control aliquot similarly.

g) Expose the loaded gels and treated control to the potential denaturing conditions for an appropriate time if different from processing in f).

h) Release the solute from the gels into an appropriate solution matching the control solution.

i) Determine the bioactivity of the released solute and the total amount of solute released (e.g. UV absorbance at 280 nm for protein).

j) From the ratio of: (activity units)/(g) of the released solute to the (activity units/(g) of the fresh control, the percentage of retention of activity can be found. Since activity can degrade simply to time, etc., the controls carried along through the test process can be used to identify reduction of activity loss by protectants relative to unstabilized solute. From the results, the optimal loading conditions for maximum activity retention can be determined.

4. Biologically Active Solutes:

Any material that is soluble may in principle be loaded with the present method. The most preferred solutes are biologically active solutes and are any substance, or mixture of substances, that are susceptible to being denatured or otherwise inactivated and that has biological and/or chemical activity when active. The term includes, but is not limited to, enzymes (either isolated or in whole cells), pesticides, insecticides and the like, proteins, polypeptides, polynucleotides, nucleoproteins, polysaccharides, glycoproteins, steroids, lipoproteins, and synthetic and biologically engineered analogs thereof, either alone or in combination. The term "protein" is art-recognized and for purposes of this invention also encompass peptides. The proteins or peptides may be any biologically active protein or peptide, naturally occurring or synthetic. Examples of proteins include antibodies, enzymes, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide-T, thyrocalcitonin, parathyroid hormone, glucagon, vasopressin, oxytocin, angiotensin I and II, bradykinin, kallidin, adrenocorticotropic hormone, thyroid stimulating hormone, insulin, glucagon and the numerous analogues and congeners of the foregoing molecules. Other examples of biologically active solutes that might be utilized in a controlled delivery application of the invention include literally any hydrophilic or hydrophobic biologically active solute. Furthermore, biologically active solutes that are liquids or are not liquid at body temperature can be incorporated into gels. Moreover, peptides and proteins which may normally be lysed by tissue-activated enzymes such as peptidases, can be passively protected in gels as well. The term, "biologically active solute" includes pharmacologically active substances that produce a local or systemic effect in animals. The term thus means any substance intended for use in the diagnosis, cure, mitigation, treatment or prevention of disease or in the enhancement of desirable physical or mental development and conditions in an animal. The term "animal" used herein is taken to mean mammals such as primates, including humans, sheep, horses, cattle, pigs, dogs, cats, rats and mice. The method is not restricted to mammals since the methods and compositions described herein may be used in literally for living entity including plants, insects, fish and the like.

Using the methods described herein, one of ordinary skill in the art may readily determine if a particular biologically active solute has the ability to be loaded into a gel and, once loaded and released, whether it retains its biological activity. The kind and manner of testing needed to determine whether a solute released from a loaded gel is biologically active will necessarily vary with the solute and is well within the level of ordinary skill in the art.

Classes of biologically active solutes which can be loaded into crosslinked gels using the methods of this invention include, but are not limited to, anti-AIDS substances, anti-cancer substances, antibiotics, anti-vital substances, enzyme inhibitors, neurotoxins, opioids, hypnotics, antihistamines, immunosuppresents (e.g., cyclosporin), tranquilizers, anti-convulsants, muscle relaxants and anti-Parkinson substances, anti-spasmodics and muscle contractants, miotics and anti-cholinergics, immunosuppressants (e.g. cyclosporine) anti-glaucoma solutes, anti-parasite and/or anti-protozoal solutes, anti-hypertensives, analgesics, anti-pyretics and anti-inflammatory agents (such as SNAID's), local anesthetics, ophthalmics, prostaglandins, anti-depressants, anti-psychotic substances, anti-emetics, imaging agents, specific targeting agents, neurotransmitters, proteins and cell response modifiers.

A more complete listing of classes of solutes suitable for loading into polymers using the present methods may be found in the *Pharmazeutische Wirkstoffe*, ed. A. Von Kleemann and J. Engel, Georg Thieme Verlag, Stuttgart/New York, 1987, incorporated herein by reference.

Anti-AIDS substances are substances used to treat or prevent Autoimmune Deficiency Syndrome (AIDS). Examples of such substances include CD4, 3'-azido-3'-deoxythymidine (AZT), 9-(2-hydroxyethoxymethyl)-guanine acyclovir (acyclovir), phosphonoformic acid, 1-adamantanamine, peptide T, and 2',3' dideoxycytidine.

Anti-cancer substances are substances used to treat or prevent cancer. Examples of such substances include methotrexate, cisplatin, prednisone, hydroxyprogesterone caproate, medroxyprogesterone acetate, megestrol acetate, diethylstilbestrol, ethinyl estradiol, tamoxifen, testosterone propionate, fluoxymesterone, vinblastine, vincristine, vindesine, etoposide, teniposide, dactinomycin, daunorubicin, doxorubicin, bieomycin, plicamycin, mitomycin, hydroxyurea, procarbazine, mitotane, aminoglutethimide, mechlorethamine, cyclophosphamide, melphalan, uracil mustard, chlorambucil, busulfan, carmustine, lomusline, semustine (methyl-CCNU), streptuzocin, dacarbazine (DTIC: dimethyltriazenomidazolecarboxamide), methotrexate, fluorouracil, 5-fluorouracil, cytarabine, cytosine arabinoxide, mercaptopurine, 6-mercaptopurine, thioguanine.

Antibiotics are art recognized and are substances which inhibit the growth of or kill microorganisms. Antibiotics can be produced synthetically or by microorganisms. Examples of antibiotics include penicillin, tetracycline, chloramphenicol, minocycline, doxycycline, vanomycin, bacitracin, kanamycin, neomycin, gentamycin, erythromicin and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Anti-viral agents are substances capable of destroying or suppressing the replication of viruses. Examples of anti-viral agents include a-methyl-P-adamantane methylamine), 9-[2-hydroxy-ethoxy]methylguanine, adamantanamine, 5-iodo-2'-deoxyuridine, trifluorothymidine, interferon, and adenine arabinoside.

Enzyme inhibitors are substances which inhibit an enzymatic reaction. Examples of enzyme inhibitors include edrophonium chloride, N-methylphysostigmine, neostigmine bromide, physostigmine sulfate, tacrine HCL, tacrine, 1-hydroxy maleate, iodotubercidin, p-bromotetramisole, 10-(a-diethylaminopropionyl)-phenothiazine hydrochloride, calmidazolium chloride, hemicholinium-3, 3,5-dinitrocatechol, diacylglycerol kinase inhibitor I, diacylglycerol kinase inhibitor II, 3-phenylpropargylamine, $N^6$-monomethyl-L-arginine acetate, carbidopa, 3-hydroxybenzylhydrazine HCl, hydralazine HCl, clorgyline HCl, deprenyl HCl, L(−), deprenyl HCl,D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate,R(+), p-aminoglutethimide tartrate,S(−), 3-iodotyrosine, alpha-methyltyrosine,L-, alpha-methyltyrosine,D L-, acetazolamide, dichlorphenamide, 6-hydroxy-2-benzothiazolesulfonamide, and allopurinol.

Neurotoxins are substances which have a toxic effect on the nervous system, e.g. nerve cells. Neurotoxins include adrenergic neurotoxins, cholinergic neurotoxins, dopaminergic neurotoxins, and other neurotoxins. Examples of adrenergic neurotoxins include N-(2-chloroethyl)-N-ethyl-2-bromobenzylamine hydrochloride. Examples of cholinergic neurotoxins include acetylethylcholine mustard hydrochloride. Examples of dopaminergic neurotoxins include 6-hydroxydopamine HBr, 1-methyl-4-(2-methylphenyl)-1,2,3,6-tetrahydro-pyridine hydrochloride, 1-methyl-4-phenyl-2,3-dihydropyridinium perchlorate, N-methyl-4-phenyl-1,2,5,6-tetrahydropyridine HCl, 1-methyl-4-phenylpyridinium iodide.

Opioids are substances having opiate like effects that are not derived from opium. Opioids include opioid agonists and opioid antagonists. Opioid agonists include codeine sulfate, fentanyl citrate, hydrocodone bitartrate, loperamide HCl, morphine sulfate, noscapine, norcodeine, normorphine, thebaine. Opioid antagonists include nor-binaltorphimine HCl, buprenorphine, chlornaltrexamine 2HCl, funaltrexamione HCl, nalbuphine HCl, nalorphine HCl, naloxone HCl, naloxonazine, naltrexone HCl, and naltrindole HCl.

Hypnotics are substances which produce a hypnotic effect. Hypnotics include pentobarbital sodium, phenobarbital, secobarbital, thiopental and mixtures, thereof, heterocyclic hypnotics, dioxopiperidines, glutarimides, dimethyl isovaleramide, a-bromoisovaleryl urea, urethanes and disulfanes.

Antihistamines are substances which competitively inhibit the effects of histamines. Examples include pyrilamine, chlorpheniramine, tetrahydrazoline, antaoniline and the like.

Tranquilizers are substances which provide a tranquilizing effect. Examples of tranquilizers include chloropromazine, promazine, fluphenzaine, reserpine, deserpidine, and meprobamate.

Anti-convulsants are substances which have an effect of preventing, reducing, or eliminating convulsions. Examples of such agents include primidone, phenytoin, valproate, and ethosuximide.

Muscle relaxants and anti-Parkinson agents are agents which relax muscles or reduce or eliminate symptoms associated with Parkinson's disease. Examples of such agents include mephenesin, methocarbomal, cyclobenzaprine hydrochloride, trihexylphenidyl hydrochloride, levodopa/carbidopa, and biperiden.

Anti-spasmodics and muscle contractants are substances capable of preventing or relieving muscle spasms or contractions. Examples of such agents include atropine, scopolamine, oxyphenonium, and papaverine.

Miotics and anti-cholinergis are solutes which cause bronchodilation. Examples include echothiophate, pilocarpine, physostigmine salicylate, diisopropylfluorophosphate, epinephrine, neostigmine, carbachol, methacholine, bethanechol, and the like.

Anti-glaucoma solutes include betaxalol, pilocarpine, timolol, and combinations of timolol and its salts with pilocarpine.

Anti-parasitic, -protozoal and -fungus include ivermectin, pyrimethamine, trisulfapyrimidine, clindamycin, amphoteficin B, nystatin, flucytosine, natamycin, and miconazole.

Anti-hypertensives are substances capable of counteracting high blood pressure. Examples of such substances include alpha-methyldopa and the pivaloyloxyethyl ester of alpha-methyldopa.

Analgesics are substances capable of preventing, reducing, or relieving pain. Examples of analgesics include morphine sulfate, codeine sulfate, meperidine, and nalorphine.

Anti-pyretics are substances capable of relieving or reducing fever and anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances which have an anesthetic effect in a localized region. Examples of such anesthetics include procaine, lidocain, tetracaine and dibucaine.

Ophthalmics include diagnostic agents such as sodium fluorescein, rose bengal, methacholine, adrenaline, cocaine, and atropine. Ophthalmic surgical additives include alpha-chymotrypsin and hyaluronidase.

Prostaglandins are art recognized and are a class of naturally occurring chemically related, long-chain hydroxy fatty acids that have a variety of biological effects. Examples of such agents include E2 and E1.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Anti-psychotic substances are substances which modify psychotic behavior. Examples of such agents include phenothiazines, butyrophenones and thioxanthenes.

Anti-emetics are substances which prevent or alleviate nausea or vomiting. An example of such a substance includes dramamine.

Imaging agents are agents capable of imaging a desired site, e.g. tumor, in vivo. Examples of imaging agents include substances having a label which is detectable in vivo, e.g. antibodies attached to fluorescent labels. The term antibody includes whole antibodies or fragments thereof.

Specific targeting agents include agents capable of delivering a therapeutic agent to a desired site, e.g. tumor, and providing a therapeutic effect. Examples of targeting agents include agents which can carry toxins or other agents which provide beneficial effects. The targeting agent can be an antibody linked to a toxin, e.g. ricin A or an antibody linked to a biologically active solute.

Neurotransmitters are substances which are released from a neuron on excitation and travel to either inhibit or excite a target cell. Examples of neurotransmitters include dopamine, serotonin, q-aminobutyric acid, norepinephrine, histamine, acetylcholine, and epinephrine.

Cell response modifiers are chemotactic factors such as platelet-derived growth factor (pDGF). Other chemotactic factors include neutrophil-activating protein, monocyte chemoattractant protein, macrophage-inflammatory protein, SIS (small inducible secreted), platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor and bone growth/cartilage-inducing factor (alpha and beta).

Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin.

The present invention will now be illustrated by the following, non-limiting examples.

EXAMPLES 1

Development of Gel Sorbent in a Support Matrix

This Example illustrates creation of a gel directly in a supporting matrix of porous cellulose fiber.

The gel is a polyacrylamide and the support matrix is either filter paper or Kimwipe (trademark of Kimberly-Clark). The pregel solution is made by dissolving 5 g acrylamide (Aldrich Chem. Co., (0.133 g methylenebisacrylamide (BIS) (Aldrich Chem. Co.), and 240 microliters tetramethylethylenediamine (TEMED, Aldrich) in 100 ml deionized water. After the solution is degassed under vacuum for about 15 minutes to removed dissolved oxygen in the solution, about 40 mg ammonium persulfate (APS, Aldrich) is added as initiator. As soon as the APS is added, a piece of Kimwipe is immersed in the solution and taken out to be placed between two flat glass plates. The gelation reaction is allowed to continue for about 12 hours. The same procedure is repeated using a piece of filter paper.

After gelation, the glass plates are separated and the gel membrane peeled off. This results in a clear gel with the thickness and strength of the original porous cellulose substrate.

EXAMPLE 2

Loading, Release and Protection of Amylase

A series of experiments was performed to test loading and release of amylase from dextran gels. Dextran gel cylinders were synthesized in our laboratory. These materials had a surface area/volume ratio much smaller than dextran gel beads. We wanted to rule out the possibility that surface adsorption effects are significant in gel loading using the methods of the invention. The sample dimensions used are suitable for a controlled delivery application.

Dextran Gel Synthesis and Characterization

The dextran gels were synthesized by dissolving the dextran polymer in aqueous sodium hydroxide solution. Approximately 1 g of dextran (mol. wt. 39,100) was dissolved in 10 ml of aqueous sodium hydroxide solution (0.02M). The first dextran polymer and sodium hydroxide solution was stirred until the polymer was wetted. The solution was then covered with Parafilm and allowed to completely hydrate over the course of 24 hours.

Divinylsulfone (DVS) was added by micropipette and the solution was stirred with a spatula. The solution was kept in an ice bath so as to slow the reaction time. The solution was then placed in clean glass tubing molds (2 mm diameter× 152.4 mm length) by syringe. The amount of crosslinker used is reported as gram reagent per gram of dry polymer. The DVS dosage for the dextran gels was 0.12 g/g dextran. The molds were covered with Parafilm and allowed to completely react over a 24 hour period.

The gels were then removed from their molds by injecting some deionized water into the gel mold using a syringe. The gels were then placed in deionized water to leach out any unreacted reagents remaining in the gel. The water was changed periodically over a three-four day period. Once a constant weight was obtained, the gels were assumed to be free of any unreacted reagents. The gels were then cut into 15 mm×1.75 mm diameter pieces and placed into a desiccator jar to dry for 24–48 hours. The dry gel had dimensions of 7.15 mm×0.75 mm diameter.

The gels were characterized in terms of their degree of swelling. Since the degree of swelling is defined as the ratio of swollen gel mass to that of dry polymer mass, the dry polymer mass was assumed to be 10% (mass to volume).

Equilibrium Loading

The loading of a biologically active solute into the hydrogel was performed by equilibrating the hydrogel in a biologically active solute-containing solution. All experiments were run in triplicates. For dry gel experiments, dry gels were equilibrated with 3 ml PEG (mol. wt. 10,000, 12 wt %)/salt (0.22M KBr, KCl, or KI) or protein (about 1.00 mg amylase/ml, PEG/salt) solution. Three ml of PEG/salt or protein/PEG/salt solution were added to 3.7 ml glass vials into which the gels were placed. Three gels (12.5 mg total weight) were placed in each vial. The gel mass/solution mass ratio during loading of the dry gels was $2.55 \times 10^{-3} \pm 0.27 \times 10^{-3}$ so that the solution is in excess relative to the gel concentration. This mimics the conditions in a standard in vitro release test. The gels and vials were stored at room temperature in a desiccator jar and the weights of the gels were recorded vs. time.

A blot and dry method was used to weigh the gels. Once a constant weight was obtained, the gels were assumed to be equilibrated. Once equilibrated with the appropriate solutions, the gels were removed from solution and placed in a desiccator jar to dry. The swollen dimensions of the gels were 1.17 mm diameter×10.2 mm length. The dry gels were left in the desiccator jar until they were ready to be used.

The dry gels were equilibrated with solution prior to the protein equilibration. This is an optional step. To begin, the dry gels were equilibrated with 3 ml PEG (mol. wt. 10,000, 12 wt %)/salt (0.22M KBr, KCl, or KI). Three gels were placed in each vial. The gels remained in solution until a constant weight was obtained. This process took approximately 60 hours. At that time, the gels were removed from the PEG/salt solution and placed in the protein loading solution. The swollen weight of the gels upon removal from the PEG/salt solution was about 40 mg total weight.

To load the swollen gels, the swollen PEG/salt loaded gels were placed in a protein solution. The gel-solution ratio during the protein loading of the swollen gels was $8.28 \times 10^{-3} \pm 0.35 \times 10^{-3}$. The swollen gels were equilibrated with 3 ml of protein (about 0.20 mg ovalbumin/ml; about 1.00 mg amylase/ml) solution plus PEG/salt solution. During the swollen loading experiment, there was no salt variance, i.e., PEG/KI loaded gels were placed in protein/PEG/KI solutions. The gels remained in solution until a constant weight was obtained by the blot and weigh method.

The protein content could be estimated by mass balances in the case of the dry gel experiments. The amount of protein absorbed by the gel was assumed to be the difference between the dry loaded gel weight and the dry loaded weight of a gel treated identically but for the absence of protein in the loading solution. As for the swollen gel experiments, protein content was determined by spectrophotometric data which revealed the total amount of protein released in the sample.

Release Kinetics

The protein released from the dry gels was estimated by mass balances and calculated from spectrophotometric data while that for the swollen gels was only by spectrophotometric data. A phosphate buffer solution (0.01M with measured pH of 6.79) was used to leach out the protein from the protein loaded dry gels. Three mL of phosphate buffer was placed in each vial. At specified time intervals, a defined volume of released solution was removed from the original solution. This volume of released sample was placed in a vial. Immediately after the removal of the released sample, an identical volume of fresh phosphate buffer was placed back into the original releasing media. Therefore, a constant volume was maintained for the release experiments. This process was continued for approximately 10 hours of regulated sampling, with samples taken every 20 minutes for the first 2 hours and then every hour. This particular technique was used to determine total amount of released biologically active solute data.

For other gels, experiments were done to calculate the diffusion coefficient for the biologically active solute within the gel. A constant volume was maintained for the release experiment, as above. A constant volume of solution was removed from the release vial and placed in another vial. The gels were replenished with an exact volume of fresh phosphate buffer. This process was continued for approximately 5 hours with samples taken every 5 minutes for the first half hour, ever ten minutes the second half hour, every half hour for the second hour and then on the third and fifth hour. The released solution samples were analyzed using a spectrophotometer. The absorbencies measured were converted into amount of protein released using calibration curves.

Experiment 1: Loading and Release of amylase using buffer without any protectant or loading polymer Amylase was loaded into a dextran gel. The buffer contained 0.01M Phosphate Buffer 0.005 mol $KH_2PO_4$– (cat. #P-285, Fisher Scientific), 0.005 mol $Na_2HPO_4$, (cat. #SX0720-1, MCB Mfg. Chemists); pH 6.68 at 25 degrees C. The biologically active solute was α-amylase, *B. subtilis*, having a molecular weight of 48,450, cat. #171568, Calbiochem., 0.9866 mg amylase/ml solution. The gel was made from dextran (molecular weight 40,800, cat. #D-4133, Sigma Chemical Co.) in a 10% solution and crosslinked with 0.14 g divinyl sulfone (DVS-cat. #V370-0, Aldrich Chemical Co.)/g dry dextran.

Loaded gels were dried in a desiccator jar at room temperature. Release experiments were run as described above using a 3mL volume that was replenished with calcium chloride/phosphate buffer (0.005 mol $KH_2PO_4$, 0.005 mol $Na_2HPO_4$ and 0.01 mM $CaCl_2$); pH 6.76 at 25 degrees C.). Absorbance was measured at 280 nm on a Shimadzu spectrophotometer.

Experiment 2: Loading and Release of amylase using buffer with added KCl

Amylase was loaded into a dextran gel as in Experiment 1 except that the salt was potassium chloride (0.22M) and the amylase was 1.0666 mg/ml solution. Absorbance was measured at 280 nm on a Shimadzu spectrophotometer.

Experiment 3: Loading and Release of amylase using buffer with added PEG and KCl Amylase was loaded into a dextran gel as described except that the loading polymer was polyethylene glycol (mol. wt. 10,000, cat. #30902-8, Aldrich Chemical Co.), 12 wt % and the amylase was 1.0133 mg/ml solution. Absorbance was measured at 280 nm on a Shimadzu spectrophotometer.

Experiment 4: Retention of Activity of amylase loaded using buffer with added PEG and KCl Amylase was loaded into a dextran gel as described except that the loaded gel was dried in an oven at 60 degrees C. for 48 hours then placed in a desiccator jar at room temperature. The amylase was 1.0067 mg/ml solution. Absorbencies were measured at 280 nm on a Shimadzu spectrophotometer. Release from the gel was performed as described. Protein content of a dry gel was determined by mass balance. The amount of protein absorbed by the gel was assumed to be the difference between the dry loaded gel weight and the initial dry gel weight.

For all release experiments, the amylase released was assayed for bioactivity using a Sigma Chemical assay kit #577 [based on colorimetric measurement of the enzymatic release of p-nitrophenol from the substrate 4.6-ethylidene $(G_7)$-p-nitrophenyl $(G_1)$-α,D-maltoheptaside].

RESULTS

Table 3 lists the results of the amylase release studies. The following points are noteworthy:

protein is absorbed or released from this gel. If high amounts of a particular protectant are desired in the gel, the gel should be made to swell in this solution.

3. Loading from KCl and PEG solution leads to a significant mass increase—9.2±2.9%, about half of this being protein, the other half protectant—i.e., salt and PEG. The gel swells much less in PEG solution than in KCl or buffer, so the absolute amount of protectant absorbed is reduced. However, the system is much more selective for protein; the estimated amylase partition coefficient is 16.4±0.9.

4. For amylase released from buffer-loaded gel, the retention of activity was 72±17% of the initial amylase solution. Activity retention was poorer from the KCl-loaded gel (48±6%). Possibly the extreme salt to protein ratio was too great to protect the amylase and the protectants may possibly have dehydrated and denatured the amylase somewhat. The best activity retention was seen with the loading system PEG-KCl. With this system, retention was virtually 100%, independent of release time interval, and significantly better than the other systems.

TABLE 3

| | Release Studies of Amylase from Dextran Gels | | | | | |
|---|---|---|---|---|---|---|
| | Buffer avg of 3 trials | std. dev. | Buffer + KCl avg of 3 trials | std. dev. | Buffer + KCl + PEG avg of 3 trials | std. dev. |
| Dry Gel Wt., mg | 13.0 | 0.3 | 13.1 | 0.3 | 13.0 | 0.4 |
| Wet Loaded Gel Wt., mg | 134.3 | 2.7 | 135.5 | 5.2 | 45.3 | 1.0 |
| Swelling Degree, mg wet/mg dry | 10.3 | 0.1 | 10.4 | 0.2 | 3.5 | 0.1 |
| Dry Loaded Gel Wt., mg | 13.3 | 0.1 | 15.5 | 0.7 | 14.2 | 0.4 |
| % Mass Loading | 2.6% | 2.0% | 18.6% | 2.7% | 9.2% | 2.9% |
| wet Released Wt., mg | 130.8 | 5.7 | 122.9 | 15.0 | 127.5 | 8.9 |
| Protein Released, mg based on 280 nm absorbance | 0.345 | 0.087 | 0.113 | 0.013 | 0.753 | 0.035 |
| "Protectant" Mass, mg (mg loading - mg protein released) | −0.012 | 0.274 | 2.320 | 0.414 | 0.447 | 0.328 |
| % Protein Loading (mg/mg dry loaded gel) | 2.6% | 0.6% | 0.7% | 0.1% | 5.3% | 0.3% |
| % "Protectant" Loading (mg/mg dry loaded gel) | −0.1% | 0.2% | 14.9% | 2.0% | 3.1% | 2.3% |
| Protein Partition Coef. | 2.60 | 0.66 | 0.79 | 0.11 | 16.42 | 0.89 |
| Active Units Released | | | | | | |
| between 0–5 min. | | | 0.21 | 0.03 | 1.68 | 0.21 |
| between 5–10 min. | | | | | 0.79 | 0.19 |
| between 40–50 min. | | | | | 0.93 | 0.11 |
| between 270–390 min. | 0.29 | 0.07 | | | 1.08 | 0.07 |
| between 390–540 min. | | | | | | |
| Retention of Activity | | | | | | |
| between 0–5 min. | | | 48% | 6% | 115% | 14% |
| between 5–10 min. | | | | | 116% | 27% |
| between 40–50 min. | | | | | 102% | 12% |
| between 270–390 min. | 72% | 17% | | | 101% | 7% |
| between 390–540 min. | | | | | | |

1. Loading from buffer alone resulted in a modest protein loading ("% Mass Loading"=2.6%) due to the high swelling of the gel. Since no other solutes are added besides buffer, the mass increase after loading matches the value of protein released as measured by UV spectrophotometry); i.e. protectant loading is zero within experimental error.

2. Adding the KCl to the buffer/protein solution without also adding PEG causes a significant increase in the mass loading of the gel (18.6%), but this is due simply to non-selective sorption of the salt due to the high gel swelling alone, so that the gel retains the salt upon drying. Little Table 4 shows results of the heat inactivation experiments. Inital A and Final A are absorbance data used to calculate activity from the assay kit. The PEG-KCl loaded gel is seen to stabilize the amylase against heat denaturation, as the gels could be dried in the oven at 60° C. and stored there for at least 2 days and still retain about 80% of its activity. In contrast, an amylase solution was completely denatured after 20 hr at this temperature (data not shown).

TABLE 4

Amylase Release from Amylase-PEG-KCl Loaded Dextran Gel, dried by heating for 48 h at 60° C.; amylase release into buffer.

| Vial | rel. time (min) | initial A | final A | Activity (U/L) | Units | Conc. (mg/ml) | Mass (mg) | U/mg | % Activity Ret'd |
|---|---|---|---|---|---|---|---|---|---|
| 4E | 5 | 0.039 | 0.122 | 290.71 | 0.87 | 1.68E-02 | 50.400 | 17.3 | 86.1% |
| 7E | 5 | 0.035 | 0.123 | 308.22 | 0.92 | 2.09E-02 | 62.700 | 14.7 | 73.4% |
| 4.1 | 5 | 0.035 | 0.107 | 252.18 | 0.76 | 1.54E-02 | 46.200 | 16.4 | 81.5% |
| | | | | | | | | avg: | 80.3% |
| | | | | | | | | std. dev: | 6.4% |

FIG. 1 is representative of the amylase release curves based on UV measurement of total protein released. The curve shows good trial-to-trial consistency of release. It is a classic diffusion controlled release curve that is linear when release is plotted here in normalized fashion against the square root of time. There is a slight lag time initially due to the fact that the gel must absorb some water first before the protein can be released. The diffusion coefficient of the protein release is of the order $5 \times 10^{-8}$ cm$^2$/sec, which is the order of magnitude expected for a large molecule like amylase in a gel.

EXAMPLE 3

Loading and Release of Ovalbumin

About 23 mg ovalbumin/ml PEG/salt solution were loaded into dextran gels using the procedures outlined in Example 2, except that in some experiments, the gels were not dried.

The partition coefficient, K, for ovalbumin is equal to the concentration of protein in the gel divided by the concentration of protein in solution. In this particular study, the concentration of protein in the gel reflects the amount of solute which has been released; therefore, all protein released into the buffer solution is assumed to be the amount absorbed by the gel. This allowed for an estimate of the partition coefficients. Partition coefficients ranged from 3.4 to 6.9, depending on salt and protein concentration.

From ovalbumin calibration curves, the absorbance vs. time data was converted into concentration vs. time data. The amount of protein released in 3 ml buffer was calculated as the total volume of buffer solutions (3 mL) multiplied by the concentration at a particular instant. Finally, the total amount of protein released is determined as a function of time. The total amount of protein released is the amount of protein released at a specific time interval. ($t_n$) plus the sum of the amount of protein removed at all previous time intervals (not including $t_n$). Release kinetic data (not shown) revealed diffusion-controlled release kinetics, similar to the amylase curve in FIG. 1.

The weight percent of loaded protein was calculated using the spectrophotometric data. It is the total amount of protein released from the gel divided by the weight of the dry gel or the swollen gel. The average estimated percent loadings ranged from 0.31±0.01 mg protein/mg initial dry gel for KCl loaded gels to 0.38±0.01 mg protein/mg initial dry gel for KBr loaded gels. Loadings of the protectant salt and polymer were ranged from about 0.02 to 0.10 mg protectant/mg initial dry gel. The swollen gels show a slightly higher weight percentage than the dry gels.

Mass balance calculations were also performed assuming that sorption of salt equals the PEG and salt uptake into the gel. We subtracted this value from the weight of the protein, PEG and salt-loaded gel. Loading calculated using mass balance ranged from 0.35 to 0.43 mg protein/mg dry gel, in reasonable agreement with the spectrophotometric data.

EXAMPLE 4

Loading and Release of Ovalbumin from HPC Gels

A series of experiments was performed to test loading and release of ovalbumin from a responsive hydroxypropylcellulose gel.

A. Synthesis of pH-Responsive HPC Disks

The crosslinking reaction of HPC with adipoyl chloride was performed as follows: Exactly 50 ml of N-methyl pyrolidone (Fisher Scientific, Catalog No. 03688-4) was added to 5 grams of hydroxypropylcellulose (Aqualon, Klucel 99-EF NF). The two materials were mixed on a magnetic stirrer for about 2 hours, while covered, to achieve a clear and colorless solution. This solution was then placed in a refrigerator for about 1 hour in order to achieve a solution temperature of 4°–8° C. To this solution, while stirring, 1 mL of cold (2°–8° C.) adipoyl chloride (Aldrich, Cat. No. 16,521-2) was added, and the resulting solution allowed to stir for 1 minute. After the addition of adipoyl chloride, the mixture was poured into molds consisting of two glass plates separated by a 2-mm thick buna rubber spacer. The crosslinking was allowed to proceed for 24 hr at room temperature. After the crosslinking reaction, the gel sheet was cut into disks 12.5 mm diameter with a cork borer, and washed in a vessel containing an excess of deionized water (Millipore Alpha-Q). After about 8 hours the water is decanted off, and the vessel filled with methanol (ACS grade). The gel is allowed to sit in methanol solution for 5 hours. This is followed by three more, 5 hour methanol washes.

The HPC gel made in this way was pH responsive. This was tested by making an HPC cylinder with the same reagents but using a pipette as a mold. The pipette was mounted in an airspace of a small, clear capsule (about 5 cm×4 cm×2 cm). Temperature of the capsule was regulated by equilibrating it with well stirred, temperature controlled water solution. A differential thermocouple arrangement permitted the monitoring of temperature differences between water and air within the capsule to about 0.005 deg. C. Water temperature within the capsule was measured to about 0.1 deg. C. with a digital thermocouple (mfg. by Cole-Parmer Scanning Thermocouple Thermometer #2800-00). Two sealed containers were partially filled with pure, degassed distilled water. One container also contained a port to allow addition of acid; the second container contains a port for addition of base. Use of a single container to generate a wide range of pH values from acid to base would lead to formation of neutral salt, which might have induced a volume change in the gel. A series of pH solutions was made, as described below, and then pumped through the bore of the tube at a flow rate of 3 ml/min. The diameter of the gel cylinder was observed at each pH and recorded through the optically clear walls of the capsule using a 10× microscope. Volumetric ratio changes of the gel with pH were determined by cubing the ratio of the gel string diameter to pipette bore. The pH solution was changed every 0.5 pH units and maintained to let the gel reach equilibrium. Then, the volume of the gel was measured. Water temperatures differed by no more than 0.1 degree C. during the experiments and were maintained at 25 degrees C. Low pH values were obtained by adding concentrated hydrochloric acid in increasing amounts to the pure, distilled water in one container. Above the pH value for pure, distilled water lacking any acid addition (pH 6), the second container was employed and sodium hydroxide (1N) was added. The pH was controlled by flowing dry nitrogen gas slowly through the headspace of each container to maintain a positive pressure and prevent entrance of ambient air into the container. pH was recorded continuously in each container by an Orion combination pH electrode (#91-56) immersed in the solution connected to an Orion #520 pH meter. This gel exhibited a volumetric dependency on pH.

A general method of gel disc preparation has been described by Antonsen, et al. (K. P. Antonsen, et al., *Biomat, Art. Cells & Immob. Biotech*, 21(1), 1–22 (1993)).

B. Loading of Ovalbumin

The materials used were:

Buffer: $KH_2PO_4/Na_2PO_4$ (Buffer Salt, pH 6.86, Fisher Scientific, #78). Protein: Ovalbumin Grade II (A5253) Sigma Chemical (St. Louis, Mo.); 2.3 mg protein/mL soln.

Second Polymer: Polyvinyl Alcohol 87–89% hydrolyzed, Aldrich Chemical (36, 317-0) 10% by weight in loading soln.

Salt: No salt used

The loading of ovalbumin into the gel was performed by equilibrating the gel in an ovalbumin solution. Ten ml of PVA or ovalbumin/PVA solution were added to 2.0 ml glass vials into which the HPC gels were placed. One gel (3.5 mg total weight) was placed in each vial. The gels and vials were stored at room temperature in a desiccator jar and the weights of the gels were recorded vs. time. A blot and dry method was used to weigh the gels. Once a constant weight was obtained, the gels were assumed to be equilibrated. Once equilibrated with the appropriate solutions, the gels were removed from solution and placed in a desiccator jar to dry.

The ovalbumin content was determined solely by mass balances. The amount of ovalbumin absorbed by the gel was assumed to be the difference between the dry loaded gel weight and the initial dry gel weight for gels loaded with, and without, PVA.

From mass balance calculations, the average percentage loading (n=3) of HPC gels with PVA, ovalbumin and buffer was 135.5%±8.1%. The average percentage loading (n=3) of HPC gels without PVA was 38.3%±21.5%. The estimated ovalbumin loaded is the difference between these numbers, or about 97%. Thus, almost all of the ovalbumin was loaded into the HPC gels.

Release Kinetics

The ovalbumin released from the dry gels was determined as follows: The phosphate buffer solution was used to leach out the ovalbumin from the ovalbumin-loaded gels. Three ml of phosphate buffer was placed in glass vials. At specified time intervals, a defined volume of released solution was removed from the original solution. This volume of released sample was placed in a vial. Immediately after the removal of the released sample, an identical volume of fresh phosphate buffer was placed back into the original releasing media. Therefore, a constant volume was maintained for the release experiments. This process was continued for approximately 10 hours of regulated sampling, with samples taken every 20 minutes for the first 2 hours and then every hour. This particular technique allowed for assay of total amount of released ovalbumin.

Release of ovalbumin into phosphate buffer after 24 hr was equal to 8 mg, or 23 mg/mg dry weight gel.

EXAMPLE 5

Loading and Release of Amylase from HPC Gels

The loading of α-amylase into HPC gels was performed by the same method as for ovalbumin with the following reagents.

Buffer: $KH_2PO_4/Na_2PO_4$ (Buffer Salt, pH 6.86, Fisher Scientific, #B78).

Protein: α-amylase, bacillus subtilis; mol. wt. 48,450; Calbiochem 1,000,000 units (cat #171568); 1.37 mg amylase/mL, soln.

Loading Polymer: PEG-PPG Copolymer (50/50 by weight), Pluronic P105, mol. wt. approx. 6,500 (BASF Performance Chemicals), 10% by weight in loading soln.

Salt: KI, ACS grade (Fisher Scientific, Cat. #P410), 0.22M.

Gels were loaded as above and then dried in desiccator at room temperature.

The release of α-amylase from HPC gels was performed by placing the dried gels in 3 mL release buffer (release buffer=0.005M $KH_2PO_4$, 0.005M $Na_2PO_4$, 0.01M $CaCl_2$) in glass vials. These vials were hand shaken initially and at various intervals during release. At timed intervals, the liquid was carefully removed from the vials and replaced with fresh buffer.

A bioactivity assay was performed using a Sigma Chemical Assay Kit #577 (based upon colorimetric measurement of the enzymatic release of p-nitrophenol from the substrate 4,6 ethylidene ($G_1$)-p-nitrophenol ($G_1$)-α, D-maltoheptaside). The concentration assay for amylase is run using a UV/VIS spectrophotometer (Shimadzu 160 U) at 280 nm. The bioactivity of the α-amylase was determined at selected intervals, and the concentration of the enzyme was assayed at all intervals.

Characteristic release curves for α-amylase from the HPC gel (not shown) revealed a diffusion-controlled release pattern with release as a function of the square root of time showing a linear relationship. The released enzyme maintained at least 40% of its original bioactivity over the release interval of 24 hours.

B. Utilities/Formulations

Polymer networks of the invention loaded with a solute (i.e., a biologically active solute) and its appropriate protectants find use as delivery vehicles in agricultural, pharmaceutical or veterinary applications. The techniques described herein may be used to load oral dosage forms (i.e., tablets), injectable gel microspheres, reservoirs of transdermal devices and the like. In one embodiment of the present drug delivery method, a responsive gel is loaded with a biologically active solute and a protectant moiety at one temperature using the method of the invention and undergoes a volumetric change (i.e., expansion or collapse) to deliver the entrained biologically active solute at another temperature. Delivery of the solute may be modulated by a temperature higher than the temperature of the gel in its loading mode (See Gutowska et al., *J. Controlled Release*, 22:95–104 (1992), using NIPA to release heparin at high temperature). In another embodiment, a gel that is not a responsive gel is loaded using the present methods and simple passive diffusion of solute out of the gel provides the necessary release.

In a further drug delivery embodiment, a loaded responsive gel expands to release a drug during exposure to pH conditions that are different than the pH conditions to which it is exposed in the loading mode. Without wishing to be bound by any theory, a loaded cellulose ether gel such as HPC with an LCST near body temperature (e.g., 42° C.) should have its LCST shifted to a lower temperature at lower pH. This is because very few —COOH and/or —OH groups are ionized at low pH and the gel would tend to have a reduced hydrophilicity. At higher pH, many —COOH and/or —OH groups will be ionized and the LCST is shifted to a higher temperature due to increased hydrophilicity. Around body temperature, the gel is therefore very sensitive to pH change and would be collapsed at low pH (i.e., that of the stomach, where the drug would be retained within the polymer network) and expanded at higher pH (i.e., that of the intestine, where the polymer network would expand and release the drug). A reversible gel may be made from starting materials (i.e., cellulose ethers of various configurations) that vary in their hydrophobic/hydrophilic nature when ionized, so that the methods described herein may be used to make a loaded, reversibly responsive, pH-sensitive gel with an LCST designed to match the application. The LCST of cellulose ethers is well known and can be easily determined and verified. Exemplary LCST's (degrees C.) are 49° (MEC); 42°–46° (HPC); 59° (methyl(hydroxypropyl)cellulose); 60° methyl(hydroxyethyl)cellulose; and 55°–70° (ethyl(hydroxyethyl)cellulose).

Loaded polymer networks of the invention may be used to coat medical devices to improve the surface properties and to incorporate a desirable medicament into the coating.

Loaded polymer networks of the present invention also find use in the agricultural release of pest control substances (i.e., solutes) such as pesticides, pheremones, fungicides and herbicides, including viruses and bacteria. Various controlled release devices or encapsulation products may be used with the loaded gels of the invention that are adapted to deliver a cleaning substance, selected enzymes, detergents, or bleaches. When the loaded responsive polymer gels are chosen so that they are capable of delivering a substance into organic solvents, such as paints or similar products, controlled release devices comprising the polymer gel networks of the invention may be formulated.

Loaded polymer networks of the present invention also find use as wound dressings. For example, a medicament like hyaluronic acid, along with one or more protectants, may be loaded into a polymer network that itself is incorporated into a bandage, gauze or other conventional wound dressing. Upon activation by an appropriate environmental trigger such as a temperature change or a change in pH, the gel delivers the entrained medicament to the wound environment. If the gel is triggered to expand and release the medicament, it may also incorporate wound exudates at the same time.

Loaded polymer networks of the invention also find use as iontophoretic devices. Iontophoretic function of a polymer network of the invention may conveniently be studied in vitro in a commercially available Franz-type transport cell. A polymer network of the invention is loaded with a drug according to procedures described herein. The loaded gel is placed in the reservoir of a well type electrode. The upper (donor) portion of the cell is separated from the buffer-filled bottom (receptor) portion by a membrane (e.g., porcine skin or a synthetic membrane). In a typical protocol, current is applied to the anode which drives the positively charged drug through the membrane into the receptor solution. The amount of drug in the receptor solution is assayed using, for example, HPLC.

Polymer networks and biologically active solutes and protectants that are loaded within the network may be used in pharmaceutically-effective amounts, with or without a compatible carrier. The term "carrier" includes any liquid, gel, capsule, fluid, ointment, cream, lotion or the like, which is encapsulates or otherwise incorporates the loaded gels of the present invention. Carriers should be suitable for use in, or on a subject and should not interact with components of the polymer network in a deleterious manner. The term "compatible", as used herein, means that the components of the pharmaceutical compositions are capable of being commingled with the polymer network of the present invention, and with each other, in a manner such that there is no interaction which would substantially reduce the pharmaceutical efficacy of the pharmaceutical. A "pharmaceutically-effective amount" of a biologically active material or polymer network containing the material is that amount which produces a result or exerts an influence on the particular condition being treated.

Some examples of substances which can serve as pharmaceutically-acceptable carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such a peanut oil, cottonseed oil, sesame oil, olive oil, corn oil and oil of theobroma; polyols such as propylene glycol, glycerine, sorbitol, mannitol, and polyethylene glycol; sugar; alginic acid; pyrogen-free water; isotonic saline; phosphate buffer solutions; cocoa butter (suppository base); emulsifiers, such as the Tweens [Registered TM]; as well as other non-toxic compatible substances used in pharmaceutical formulations. Wetting agents and lubricants such as sodium lauryl sulfate, as well as coloring agents, flavoring agents, excipients, tableting agents, stabilizers, antimicrobials, antioxidants, and preservatives, can also be present. Other compatible pharmaceutical additives and actives (e.g., NSAID's; pain killers; muscle relaxants) may be included in the pharmaceutically-acceptable carrier for use in the compositions of the present invention. For example, local anesthetics (e.g., benzyl alcohol; lidocaine) may be included in the pharmaceutically-acceptable carrier.

The formulations include, but are not limited to, those suitable for oral, buccal, rectal, topical, nasal, ophthalmic or parenteral (including subcutaneous, intramuscular and intravenous) administration, all of which may be used as routes of administration for practicing the present invention. Other suitable routes of administration include intrathecal administration directly into spinal fluid (CSF), direct injection onto an arterial surface to prevent re-stenosis, and intraparenchymal injection directly into targeted areas of an organ.

Formulations of the present invention suitable for oral administration may be presented as discrete units such as capsules, cachets, tablets or lozenges, each containing a predetermined amount of the potentiating agent as a powder or granules; as liposomes containing a loaded gel; or as a suspension in an aqueous liquor or non-aqueous liquid such as a syrup, an elixir, an emulsion or a draught.

Formulations suitable for parenteral administration conveniently comprise a sterile aqueous preparation of the active solute, which is preferably isotonic with the blood of the recipient.

Nasal spray formulations comprise purified aqueous solutions of the active solute with preservative agents and isotonic agents. Such formulations are preferably adjusted to a pH and isotonic state compatible with the nasal mucous membranes.

Formulations for rectal administration may be presented as a suppository with a suitable carder such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

In addition to the aforementioned ingredients, the formulations of this invention may further include one or more accessory additives incorporated into the gel selected from diluents, buffers, biocides (e.g., chlorhexidine gluconate, triclosan, povidineiodine, and the like), adhesives (e.g., lectin, pectin, fibronectin, and the like), flavoring agents, binders, anti-microbials, skin permeation enhancers, disintegrants, surface active agents, thickeners, lubricants, preservatives (including antioxidants), protectants (e.g., sugars, amino acids, nonionic surfactants) and the like.

The pharmaceutical compositions may be in the form of a sterile injectable aqueous or oleaginous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectibles.

Equivalents

It will be understood that the preceding is merely a description of certain preferred embodiments of the present invention. It will be readily apparent to one of ordinary skill in the art that various modifications can be made without departing from the spirit or scope of the invention. Modifications and equivalents are therefore within the scope of the invention.

What is claimed is:

1. A method of loading a solute into a crosslinked polymer gel network, comprising:
   providing the crosslinked polymer gel network, including a solvent;
   selecting a loading polymer that is soluble in the solvent and is capable of facilitating selective partitioning of the solute into the gel network; and
   contacting the solvent-including crosslinked polymer gel network with a solution containing:
   the solute; and
   the loading polymer the contacting being performed under conditions sufficient for the solute and the loading polymer to selectively partition into the gel network and for the solute to retain activity while in the gel network.

2. The method of claim 1, wherein the step of contacting further comprises contacting the crosslinked polymer gel and the solute with a salt, under conditions sufficient for the salt to enhance partitioning of the solute into the gel relative to partitioning without the salt.

3. The method of claim 2, wherein the solute is partitioned into the gel with a partition coefficient of greater than 1.

4. The method of claim 2, wherein the retention of the activity of the solute is at least 100%.

5. The method of claim 1, wherein the step of contacting comprises contacting with a crosslinked polymer gel network that is obtainable from one of a group of water soluble polymeric precursor materials that separate into two or more aqueous phases when combined with another polymer of the group.

6. The method of claim 5, wherein the group of water soluble polymeric precursors consists of polyethylene oxide, polyethylene glycol, polyvinylalcohol, methylcellulose, dextran, hydroxypropyldextran, ethylhydroxyethylcellulose, polyvinylpyrolidone, hydroxypropylcellulose, hydroxpropylstarch, polypropylene glycol, polysucrose, carboxymethylcellulose, carboxymethyldextran, dextran sulfate, and methoxypolyethylene glycol.

7. The method of claim 6, wherein the step of contacting comprises contacting with a biologically active solute having a molecular weight of at least 1000.

8. The method of claim 1, wherein the step of contacting comprises contacting with a gel that is responsive to a change in an environmental condition to which the gel is exposed.

9. The method of claim 8, wherein the change in environmental condition comprises a change in a condition selected from the group consisting of temperature, electric field, photon energy, pH, solvent composition, ion concentration, concentration of biologically active solute and pressure.

10. The method of claim 1, wherein the step of contacting comprises contacting with a biologically active solute.

11. The method of claim 10, wherein the biologically active solute is an enzyme.

12. The method of claim 1, wherein the step of selecting comprises determining a value Q corresponding to a swelling degree of the gel network in the loading polymer solution and a value k corresponding to a partition coefficient for the loading polymer in the loading polymer solution.

13. The method of claim 12, wherein the values of Q and k are selected from a phase diagram.

14. A method of loading a solute into a crosslinked polymer gel network, comprising:
   providing the crosslinked polymer gel network, including a solvent;
   selecting a loading polymer that is soluble in the solvent and is capable of facilitating selective partitioning into the gel network at least 10% mass solute/mass polymer gel network; and
   contacting the solvent-including crosslinked polymer gel network with a solution containing:
   the solute; and
   the loading polymer,
   the contacting being performed under conditions sufficient for at least 10% mass solute/mass polymer gel network to selectively partition into the gel network.

15. The method of claim 14, wherein the solute has a molecular weight of at least 1000.

* * * * *

UNITED STATES PATENT AND TRADEMARK OFFICE
CERTIFICATE OF CORRECTION

PATENT NO. : 5,603,955
DATED : February 18, 1997
INVENTOR(S) : Stevin H. Gehrke, E.C. Lupton, Matthew E. Schiller, Lorelle Uhden and Nitin Vaid It is certified that error appears in the above-indentified patent and that said Letters Patent is hereby corrected as shown below:

Column 2, line 7: after "loadings"; please delete ";" and insert therefor --(--.

Column 2, line 8: after "mass"; please delete ","  and insert therefor --)--.

Column 2, line 40: after "contacting"; please delete "of".

Column 15, line 32: before "can"; please insert --one--.

Column 15, line 32: after "can"; please delete "one".

Column 20, line 17: delete "EXAMPLES"; please insert therefor --EXAMPLE--.

Column 26, line 63: delete "#2800-"; please insert therefor --#92800- --.

Column 30, line 17: before "encapsulates"; please delete "is".

Column 31, line 13: delete "carder"; please insert therefor --carrier--.

Column 31, line 63, after "polymer", insert --,--.

Signed and Sealed this

Twelfth Day of August, 1997

Attest:

*Attesting Officer*

BRUCE LEHMAN

*Commissioner of Patents and Trademarks*